(12) United States Patent
Doerr et al.

(10) Patent No.: US 11,998,749 B2
(45) Date of Patent: Jun. 4, 2024

(54) IMPLANTABLE MEDICAL DEVICE

(71) Applicant: BIOTRONIK SE & Co. KG, Berlin (DE)

(72) Inventors: Thomas Doerr, Berlin (DE); Sergey Ershov, Berlin (DE); Torsten Radtke, Berlin (DE); Martin Roemer, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/767,647

(22) PCT Filed: Sep. 24, 2020

(86) PCT No.: PCT/EP2020/076643
§ 371 (c)(1),
(2) Date: Apr. 8, 2022

(87) PCT Pub. No.: WO2021/078461
PCT Pub. Date: Apr. 29, 2021

(65) Prior Publication Data
US 2022/0362551 A1     Nov. 17, 2022

(30) Foreign Application Priority Data
Oct. 21, 2019   (EP) .................... 19204317

(51) Int. Cl.
*A61N 1/36*     (2006.01)
*A61N 1/362*    (2006.01)
(Continued)

(52) U.S. Cl.
CPC .......... *A61N 1/365* (2013.01); *A61N 1/3621* (2013.01); *A61N 1/39622* (2017.08)

(58) Field of Classification Search
CPC ... A61N 1/365; A61N 1/3621; A61N 1/39622
See application file for complete search history.

(56) References Cited

U.S. PATENT DOCUMENTS

| | | |
|---|---|---|
| 6,016,447 A | 1/2000 | Juran et al. |
| 6,154,675 A | 11/2000 | Juran et al. |

(Continued)

OTHER PUBLICATIONS

International Search Report (PCT/ISA/210) and Written Opinion (PCT/ISA/237) dated Nov. 25, 2020, by the European Patent Office as the International Searching Authority for International Application No. PCT/EP2020/076643.

*Primary Examiner* — Rex R Holmes
(74) *Attorney, Agent, or Firm* — Buchanan Ingersoll & Rooney PC

(57) ABSTRACT

An implantable medical device which performs the following steps during operation: a) performing a detection of whether the implantable medical device is in an implanted state; b) if it is detected that the implantable medical device is in an implanted state, activating a first diagnostic or therapeutic function of the implantable medical device, and subsequently activating a second diagnostic or therapeutic function of the implantable medical device, wherein the second diagnostic or therapeutic function is activated only after the fulfillment of at least one activation criterion selected from the group consisting of an elapse of a first time period from the activation of the first diagnostic or therapeutic function, an elapse of a second time period from the detection that the implantable medical device is in an implanted state, and a passing of a function test.

14 Claims, 2 Drawing Sheets

(51) Int. Cl.
*A61N 1/365* (2006.01)
*A61N 1/39* (2006.01)

(56) References Cited

U.S. PATENT DOCUMENTS

| | | | |
|---|---|---|---|
| 7,113,827 B2 | 9/2006 | Silvestri et al. | |
| 7,440,801 B2 | 10/2008 | Legay et al. | |
| 2007/0162078 A1* | 7/2007 | Amblard | A61N 1/3706 607/9 |
| 2010/0305641 A1 | 12/2010 | Xi et al. | |

* cited by examiner

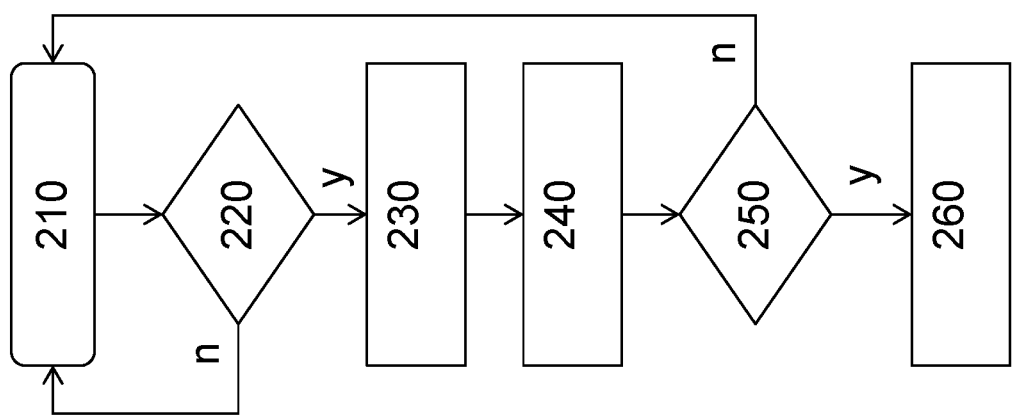

IMPLANTABLE MEDICAL DEVICE

CROSS-REFERENCE TO RELATED APPLICATIONS

This application is the United States National Phase under 35 U.S.C. § 371 of PCT International Patent Application No. PCT/EP2020/076643, filed on Sep. 24, 2020, which claims the benefit of European Patent Application No. 19204317.2, filed on Oct. 21, 2019, the disclosures of which are hereby incorporated by reference herein in their entireties.

TECHNICAL FIELD

The present invention relates to an implantable medical device according to the preamble of claim 1, a method for controlling the operation of an implantable medical device according to the preamble of claim 13, and a computer program product suitable for controlling the operation of an implantable medical device according to the preamble of claim 14.

BACKGROUND

Implantable medical devices may perform a wide variety of tasks. It is often pertinent to know when an (active) implantable medical device was actually implanted in a patient. This is because, typically, the most important functions of the implantable medical device should only be activated at the time of, or immediately after, implantation. In this way, malfunctions of the implantable medical device during transport before its implantation may be avoided. In addition, the energy consumption of the implantable medical device is reduced if functions that are particularly energy-consuming are activated only after the implantation of the implantable medical device.

For ordinary pacemakers, for example, it is known to automatically detect whether the pacemaker is already implanted. For example, U.S. Pat. No. 6,016,447 describes a pacemaker that automatically detects whether it is in an implanted state based on various measurement parameters. If it is detected that the pacemaker is in its implanted state, certain therapeutic functions that were previously deactivated are activated.

U.S. Pat. No. 7,113,827 describes an implantable medical device that emits a test stimulation pulse and measures a corresponding pulse signal and examines it more closely in the context of a signal analysis. The measured pulse width is then used to determine whether an electrode is connected to the implantable medical device. Within the scope of the signal analysis, it is also possible to determine the type of electrode connected.

U.S. Pat. No. 7,440,801 describes an implantable medical device that regularly monitors its own energy consumption. If the energy consumption increases, tests are performed to determine whether an electrode is connected to the device. If a connected electrode is detected, therapeutic functions of the implantable medical device are activated.

All of these solutions known from the prior art provide for a simultaneous activation of the possible therapeutic functions. There are, however, numerous implantable medical devices which may perform functions that are medically particularly sensitive and that are still manually activated in implantable medical devices currently being sold on the market.

In the case of implantable cardioverters/defibrillators (ICDs) or devices for performing cardiac resynchronisation therapy (CRT-D), for example, an employee of the implant manufacturer is routinely present during the implantation in order to activate the defibrillation function of the device by means of a programming device at the time of implantation. This procedure is relatively complex, since the programming device is a non-sterile device and must therefore not be located in the operating room. Instead, the programming device is operated by a trained user in a non-sterile area, while the physician who implants the ICD or CRT-D is in the sterile operating area.

A problem addressed by the present invention is that of providing a simplified means of activating medically particularly sensitive functions of an implantable medical device without requiring the presence of an additional user of a programming device in addition to the implanting physician.

The present disclosure is directed toward overcoming one or more of the above-mentioned problems, though not necessarily limited to embodiments that do.

SUMMARY

An obvious solution to this objective technical problem would be to provide a (sterile) remote control for a programming device, which could be operated directly by the implanting physician himself. However, the present invention takes a completely different approach. According to the claimed invention, at least the objective technical problem is solved by enabling a time-delayed activation of different diagnostic or therapeutic functions of the implantable medical device. The automatic activation of medically particularly sensitive or relevant diagnostic or therapeutic functions is only implemented after the implanted state of the implantable medical device has already been detected and after an additional activation criterion has been fulfilled.

Specifically, at least the problem is solved by an implantable medical device having the features of claim 1. Such an implantable medical device comprises a processor and a memory unit. The memory unit comprises a computer-readable program that causes the processor to perform the steps explained below when run on the processor.

First of all, a detection is performed in order to determine whether the implantable medical device is in its implanted state. Numerous different procedures are already known from the prior art for this basic detection of the implanted state of the implantable medical device.

If the implantable medical device is detected as being in its implanted state, a first diagnostic or therapeutic function of the implantable medical device is activated. If an additional activation criterion is fulfilled, a second diagnostic or therapeutic function of the implantable medical device is then activated in addition to the first diagnostic or therapeutic function. According to the present invention, the activation criterion is the elapse of a first time period from the activation of the first diagnostic or therapeutic function and/or the elapse of a second time period from the detection that the implantable medical device is in an implanted state and/or the passing of a function test of the implantable medical device.

Thus, in a first operating state of the implantable medical device, it is sufficient for the activation of the second diagnostic or therapeutic function if a predefined or predefinable time (optionally starting at different events) has elapsed. This is because it may then regularly be assumed that the implantable medical device is in the desired implanted state, i.e. that, for example, all electrodes of the implantable medical device are correctly positioned and may fulfill their function of influencing the body of the patient in whom the implantable medical device has been implanted.

In a second operating state of the implantable medical device, on the other hand, a function test is performed. This allows different functions of the implantable medical device to be tested before the second diagnostic or therapeutic function is activated. In this way, it is positively checked that the implantable medical device is not only in its implanted state, but that it may additionally also, for example, enter into certain desired interactions with the body of the patient in whom the implantable medical device has been implanted. The function test may also be a function test within the device itself that does not take into account any specific interaction with the body of the patient in whom the implantable medical device has been implanted.

Lastly, in a third operating state of the implantable medical device, a combination of the first operating state and of the second operating state is conceivable. In this operating state, the second diagnostic or therapeutic function may thus only be activated if both a predefined or predefinable time has elapsed and, in addition, a function test of the implantable medical device has been successfully passed.

In this way, it is possible, for example, that after automatic detection of the implanted state of the implantable medical device, a normal pacemaker function is initially activated as the first diagnostic or therapeutic function. This ensures basic level of care for the patient in question. By contrast, a shock function (defibrillation function) of the implantable medical device is only activated after a certain time has elapsed and/or after the passing of a test to determine whether the electrodes of the implantable medical device are actually correctly positioned and stimulation pulses are delivering the desired response signals. This is to prevent an undesirable premature triggering of the second diagnostic or therapeutic function during the implantation of the implantable medical device. Such a premature triggering would be conceivable, for example, if the implantable medical device, due to the particular circumstances of the implantation, for example, were to make a false diagnosis of the medical condition of the patient in whom the device has been implanted and as a result were to activate a serious medical function, such as a cardiac defibrillation function.

In the case of an implantable cardioverter/defibrillator or an implantable device for performing cardiac resynchronisation therapy, with the aid of the implantable medical device claimed in the present case there is no longer any need for the presence of an additional programming device at the time of implantation of the implantable medical device in order to manually activate the defibrillation function or any other second diagnostic or therapeutic function. This significantly reduces the outlay both for equipment and for personnel required for the implantation of a corresponding implantable medical device. At the same time, medical safety is maintained, because the second diagnostic or therapeutic function is only activated when the corresponding activation criterion is fulfilled.

In a variant, the implantable medical device has a manually actuatable device indicating the implanted state of the implantable medical device. Such a device may, for example, be a switch which is actuated during implantation by a physician who is implanting the implantable medical device. The state of the switch may then be read from the computer-readable program stored in the memory unit of the implantable medical device. This means that, even if the switch is activated manually, automatic reading and thus automatic detection of whether the implantable medical device is in its implanted state is possible.

In a variant, the detection of whether the implantable medical device is in its implanted state (implantation detection) is based on the measurement of an impedance, the measurement of a temperature, the measurement of data from an activity sensor, a signal evaluation of a test signal generated by a test stimulation pulse and/or the measurement of the energy consumption of the implantable medical device. These different methods are in themselves already known from the prior art and are described there in a manner that may be reworked by a person skilled in the art.

In a variant, implantation detection is performed by means of a cyclically performed impedance measurement at least at one electrode connection. In a variant, implantation detection is performed by means of a cyclically performed impedance measurement at the right-ventricular electrode connection.

In a variant, the implantable medical device is a pacemaker implant, a cardioverter/defibrillator (ICD), a cardiac resynchronisation therapy device (CRT-D), a spinal cord stimulator, a deep brain stimulation device or an implantable drug pump. All of these different types of implantable medical devices have different diagnostic and therapeutic functions that may be activated in a medically expedient way in a chronological sequence. For example for a drug pump, a first diagnostic or therapeutic function may be designed such that a first active substance may be delivered, while a second diagnostic or therapeutic function may be designed such that a second active substance may be delivered. It is further conceivable that, within the scope of a first diagnostic or therapeutic function, a small amount of a first active substance may be conveyed or delivered by such a drug pump, while within the scope of a second diagnostic or therapeutic function a large amount (greater than the small amount) of the same first active substance may be conveyed or delivered by the drug pump.

In the case of devices capable of performing an electrical stimulation of a specific area of a patient's tissue, the first diagnostic or therapeutic function and the second diagnostic or therapeutic function may differ, for example with regard to the type and/or strength of the electrical pulses to be delivered. In particular, if the implantable medical device is designed as an ICD or CRT-D, it is provided in a variant that the first diagnostic or therapeutic function represents or comprises an ordinary pacemaker function (i.e. in particular a function for antibradycardia stimulation of a human or animal heart), while the second diagnostic or therapeutic function represents or comprises a function for cardiac defibrillation (shock function).

In a variant, the program causes the processor to activate the first diagnostic or therapeutic function only after a third time period has elapsed from the time at which it is detected that the implantable medical device is in its implanted state. Thus, in this variant, the first diagnostic or therapeutic function is not activated immediately after the detection of the implanted state of the implantable medical device, but with a time delay. This reduces the risk of the device detecting interference signals during the implantation process and then incorrectly carrying out a certain diagnostic or therapeutic function on the basis of these signals. This is because, in this variant, the first diagnostic or therapeutic function is only actually activated if the risk of detecting such interference signals is significantly reduced due to the time that has already elapsed since the actual implantation process.

In a variant, the first time period (i.e. the time elapsed between the activation of the first diagnostic or therapeutic function and the activation of the second diagnostic or therapeutic function) and/or the second time period (i.e. the time from the detection that the implantable medical device is in its implanted state) have a length, which is between 5 minutes and 48 hours, in particular between 10 minutes and 36 hours, in particular between 15 minutes and 24 hours, in particular between 20 minutes and 12 hours, in particular between 30 minutes and 10 hours, in particular between 40 minutes and 8 hours, in particular between 50 minutes and 6 hours, in particular between 1 hour and 5 hours, in particular between 2 hours and 4 hours In a variant, the third time period (i.e. the time that elapses in a variant after detection of the implanted state until the first diagnostic or therapeutic function is activated) has a length that is also within one of the aforementioned time intervals. The first time period, the second time period and the third time period may be selected independently of each other from these time intervals. It is conceivable that the first time period, the second time period and/or the third time period are different or of the same length.

In a variant, the implantable medical device has a time-measuring device used to measure the first time period and/or the second time period. This time-measuring device may, for example, be an ordinary timer. In a variant, the time-measuring device is also used to measure the third time period. In another variant, the device has a first time-measuring device for measuring the first time period, a second time-measuring device for measuring the second time period and a third time-measuring device for measuring the third time period. By means of such a time-measuring device it is possible to record internally in the device a time which must elapse before the first diagnostic or therapeutic function or the second diagnostic or therapeutic function is activated. The implantable medical device is then not dependent on an external time signal to monitor the elapse of a corresponding time.

In a variant, the program causes the processor to stop, modify or reset the time-measuring device when a start event is detected. This manipulation of the time-measuring device may then be used to start a measurement of the first time period and/or the second time period and/or the third time period if the device is designed according to a variant in which a third time period is determined. The start event is dependent here on the type of time period to be measured. If the first time period is to be measured, the start event is the activation of the first diagnostic or therapeutic function. If the second time period is to be measured, the start event is the detection that the implantable medical device is in its implanted state. If the third time period is to be measured, the start event is again the detection that the implantable medical device is in its implanted state. Different timer ranges of the time-measuring device may be addressed by the particular state event, such that it is possible fundamentally to determine more than one time period, for example the first time period, the second time period and the third time period, at least partially simultaneously with a single time-measuring device.

In a variant, the first diagnostic or therapeutic function and/or the second diagnostic or therapeutic function comprise a detection of a cardiac signal of a patient, a stimulation of a cardiac region of a patient within the scope of a pacemaker stimulation (in particular in a right-ventricular stimulation operating mode), a stimulation of a cardiac region of a patient within the scope of a cardiac resynchronisation therapy, a function for detecting an electrode error and/or an electrode dislocation and/or a function for remote implant monitoring (so-called home monitoring). It is provided here in particular that the first diagnostic or therapeutic function comprises a detection of a cardiac signal of a patient and a stimulation of a cardiac region of a patient within the scope of a pacemaker stimulation (antibradycardia stimulation). In contrast to this, a variant provides in particular that the second diagnostic or therapeutic function comprises a stimulation of a cardiac region of a patient within the scope of a cardiac resynchronisation therapy.

In a variant, the first diagnostic or therapeutic function comprises a standard stimulation program associated with the particular type of the implantable medical device, if the implantable medical device is a cardiac stimulation device. In this case, a device-specific standard stimulation program is activated as soon as the implantation detection has been completed positively.

In a variant, diagnostic functions, automatic algorithms for antibradycardia stimulation adaptation, algorithms for electrode error detection or electrode dislocation detection and/or remote implant monitoring are activated in addition to the first diagnostic or therapeutic function, if it has been previously detected that the implantable medical device is in its implanted state.

In a variant, the first diagnostic or therapeutic function and/or the second diagnostic or therapeutic function have a function for cardiac defibrillation, a function for antitachycardia stimulation of a patient's cardiac region and/or a function for automatic adaptation of algorithms used for antitachycardia stimulation.

In a variant, the implantable medical device is designed as a device for cardiac resynchronisation therapy or as a cardioverter/defibrillator, with the second diagnostic or therapeutic function comprising a cardiac defibrillation function. Consequently, in this variant it is ensured that the defibrillation function, which typically constitutes a painful treatment of patients and should only be carried out when it is actually medically necessary, is only activated when a number of conditions are satisfied. Firstly, it must be detected that the implantable medical device is in its implanted state. Only then may the first diagnostic or therapeutic function be activated, which in this variant does not include a defibrillation function. If an additional activation criterion is now fulfilled, the second diagnostic or therapeutic function may be activated in the form of the cardiac defibrillation function, such that defibrillation of the heart of the patient in whom the implantable medical device has been implanted is then possible.

In a variant, an additional diagnostic function, a function for antitachycardia stimulation, automatic algorithms for antitachycardia stimulation adjustment, algorithms for electrode error detection or electrode dislocation detection and/or a function for remote implant monitoring are activated in addition to the second diagnostic or therapeutic function.

In a variant, the function test, the passing of which may be used as an activation criterion for the activation of the second diagnostic or therapeutic function, is a test for determining whether electrodes of the implantable medical device intended for the detection of electrical signals and/or the delivery of electrical pulses are correctly positioned, a test for determining whether electrodes intended for the detection of electrical signals and/or the delivery of electrical pulses have an electrode breakage, and/or a test for examining a signal quality criterion and/or a test for examining a type of detected physiological electrical signals.

The signal quality criterion may include, for example, the amplitude of a detected signal and/or the width of a detected signal and/or a signal stability and/or an electrode impedance. For example, different types of detected physiological electrical signals may be different cardiac signals from a patient detected by the implantable medical device (such as a QRS complex signal or the amplitude of such a QRS complex signal).

In a variant, the program causes the processor to determine shock vectors that are available for a defibrillation function after the activation criterion is fulfilled. Such a determination of shock vectors is particularly useful when a cardiac defibrillation function is selected as a second diagnostic or therapeutic function. Such shock vectors may, for example, pass between a first electrode and the housing of the implantable medical device, between a second electrode and the housing of the implantable medical device, or between a first electrode and a second electrode of the implantable medical device. The number of possible shock vectors as well as their specific design depend, among other things, on whether so-called single-coil defibrillation electrodes or so-called dual-coil defibrillation electrodes are used. The specific position of the individual electrode poles of a defibrillation electrode also has an influence on the possible available shock vectors.

In a variant, the program causes the processor to activate all of the implanted defibrillation electrodes of the implanted medical device for defibrillation and for electrode diagnostics after detecting that the implantable medical device is in its implanted state. Within the scope of the electrode diagnostics, it is determined in particular whether the electrodes are correctly positioned and whether the electrodes have an electrode fault such as an electrode breakage. This variant of activating all implanted defibrillation electrodes is particularly useful in combination with the variant of determining the available shock vectors for a defibrillation function as a second diagnostic or therapeutic function.

One aspect of the present invention relates to a method of controlling the operation of an implantable medical device, wherein this method is particularly suitable for an implantable medical device according to the above explanations. The control method comprises the steps explained below.

First of all, it is detected whether the implantable medical device is in its implanted state.

If it is positively detected that the implantable medical device is in its implanted state, a first diagnostic or therapeutic function of the implantable medical device is activated. If an activation criterion is additionally fulfilled, a second diagnostic or therapeutic function of the implantable medical device is subsequently activated. The activation criterion may be the elapse of a first time period from the activation of the first diagnostic or therapeutic function and/or the elapse of a second time period from the detection that the implantable medical device is in its implanted state and/or the passing of a function test.

One aspect of the present invention relates to a computer program product comprising computer-readable code which causes a processor to perform the steps explained below when run on the processor.

First of all, it is detected whether an implantable medical device is in its implanted state.

If it is positively detected that the implantable medical device is in its implanted state, a first diagnostic or therapeutic function of the implantable medical device is activated. If an additional activation criterion is fulfilled, a second diagnostic or therapeutic function of the implantable medical device is subsequently activated. The activation criterion may be the elapse of a first time period from the activation of the first diagnostic or therapeutic function and/or the elapse of a second time period from the detection that the implantable medical device is in its implanted state and/or the passing of a function test.

One aspect of the present invention relates to a medical method for implanting an implantable medical device. The device is implanted in a human or animal patient in need of such implantation. The implantable medical device comprises a processor and a memory unit. The implantation method is characterised by the steps explained below.

First, the implantable medical device is implanted into the patient.

Now, a detection is carried out to determine whether the implantable medical device is in its implanted state. A program running on the processor is used to do this. This may be based on measured values indicating implantation of the implantable medical device, such as a substantially constant temperature corresponding to the patient's body temperature and/or a characteristic impedance of electrodes forming part of the implantable medical device and/or a signal quality criterion of electrical signals detected by the implantable medical device.

Once the implantable medical device has been detected as being in its implanted state, a first diagnostic or therapeutic function of the implantable medical device is then activated. If an activation criterion is additionally fulfilled, a second diagnostic or therapeutic function is then activated. The first diagnostic or therapeutic function and the second diagnostic or therapeutic function are each activated by means of a program running on the processor. The activation criterion is selected here from the group consisting of an elapse of a first time period from the activation of the first diagnostic or therapeutic function, an elapse of a second time period from the detection that the implantable medical device is in its implanted state, and a passing of a function test.

All variants and alternative designs described in conjunction with the implantable medical device may be combined with one another in any way and may be transferred to the methods and computer program product described. Furthermore, the described variants of the methods may be combined with each other in any way and may be transferred to the other methods as well as to the computer program product and the device. In the same way, the described variants of the computer program product may be combined with each other in any way and may be transferred to the described methods and the described device.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further details of aspects of the present invention will be explained below in conjunction with exemplary embodiments and drawings, in which:

FIG. 2 shows a flow diagram of a method for operating an implantable medical device.

DETAILED DESCRIPTION

Figure 1:
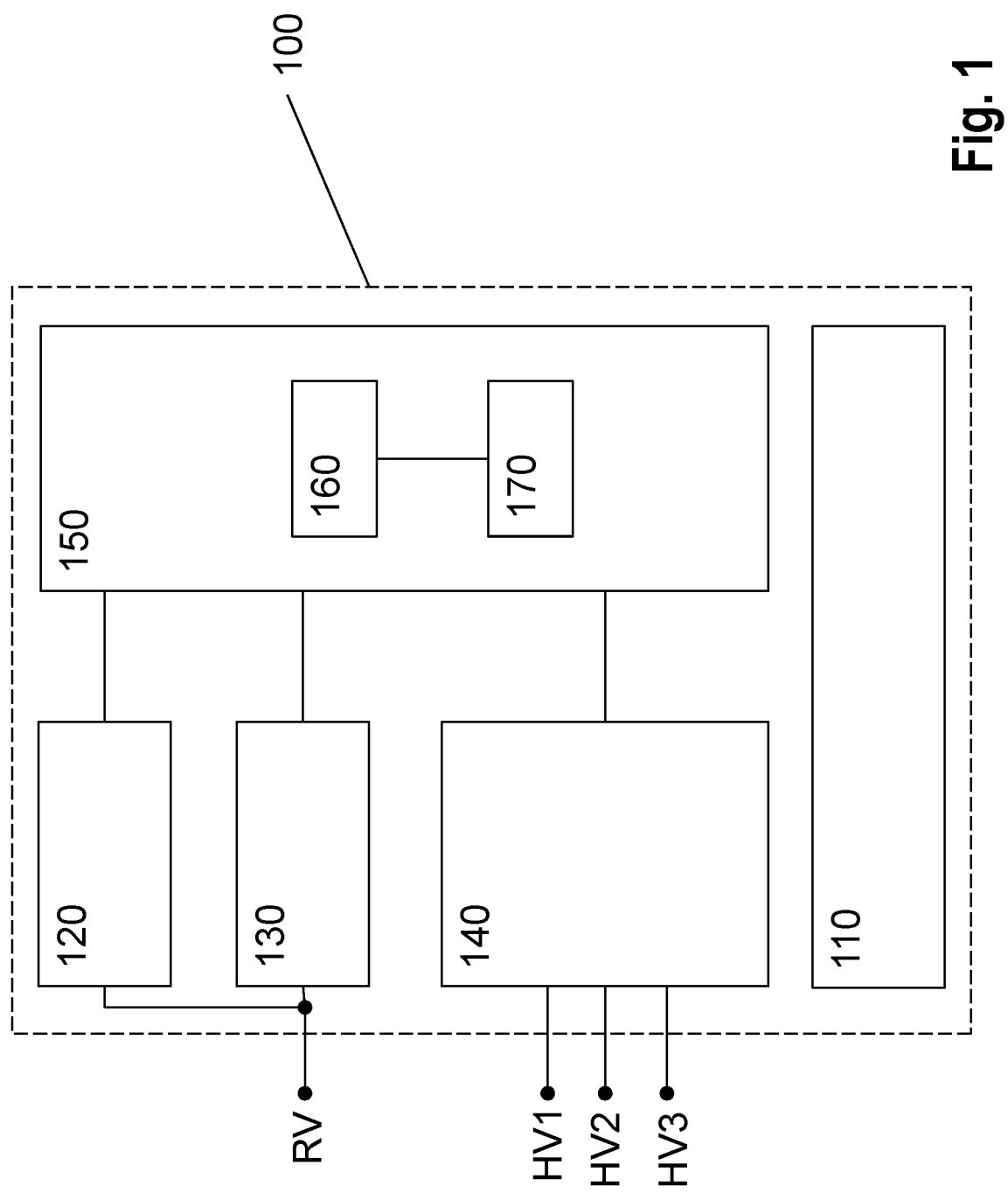
FIG. 1 shows a block diagram of an implantable medical device.

FIG. 1 shows an implantable defibrillator 100, which serves as an implantable medical device. The defibrillator 100 has an energy source 110 and an impedance-based implantation detection unit 120. This impedance-based implantation detection unit 120 is connected to a connector for a right-ventricular detection and stimulation electrode RV (RV connector). A combined detection and stimulation unit 130 is also connected to this RV connector. This combined detection and stimulation unit 130 may detect and classify the heart rhythm of a patient in whom the defibrillator 100 has been implanted. The detection and stimulation unit 130 is designed and equipped to deliver antibradycardia and antitachycardia stimulation sequences.

The defibrillator 100 also has a defibrillation unit 140 to which up to three shock electrodes HV1, HV2 and HV3 may be connected. The implantation detection unit 120, the combined detection and stimulation unit 130, and the defibrillation unit 140 are connected to a common control unit 150.

When the defibrillator 100 is delivered, only the implantation detection unit 120 is activated. This implantation detection unit 120 is able to detect the connection of an implanted right-ventricular electrode RV within a period of from 0.1 to 5 seconds and to signal this to the control unit 150. The control unit 150 then immediately activates the detection and stimulation unit 130, which performs its function as a result of this activation with a standard setting stored in a memory unit 160 of the defibrillator 100.

The memory unit 160 is operatively connected to a processor 170 and thus enables the control unit 150 to control the individual elements of the defibrillator 100.

After a waiting period of, for example, 12 hours has elapsed and a confirmation test by the implantation detection unit 120 has positively confirmed that an RV electrode has been permanently connected to the RV connector and that the signal quality of test signals recorded by the RV electrode after corresponding test stimulation pulses meets predefined criteria, the control unit 150 also activates the defibrillation unit 140. This results in the activation of a defibrillation function as a second diagnostic or therapeutic function.

At the same time, when an antitachycardia stimulation is activated by the detection and stimulation unit 130, an additional therapeutic function of this detection and stimulation unit 130 is activated. Thus, the defibrillator may now be activated by means of its detection and stimulation unit 130 both on the basis of a standard setting, which typically comprises an antibradycardia stimulation, and with an antitachycardia stimulation. In addition, the defibrillator 100 may be used to perform defibrillation if necessary for the patient.

FIG. 2 shows a schematic flow diagram of an automatic activation of two different diagnostic or therapeutic functions of an implantable defibrillator, for example the defibrillator 100 of FIG. 1.

First, a cyclically performed electrode impedance measurement 210 is used to test whether an implanted RV electrode is connected to the defibrillator and may be detected. If the result 220 of this cyclically performed electrode impedance measurement 210 is positive, a simple antibradycardia pacemaker function 230 is activated. In addition, a confirmation phase 240 is automatically initiated, during which a test is performed for a predefined time to determine whether an implanted RV electrode is still present and whether suitable signal conditions for safe defibrillator activation are present. If both conditions are satisfied after the predetermined time has elapsed, a decision step 250 is followed by an activation of the defibrillation function 260 of the defibrillator. Once the defibrillation function has been activated, the system does not test again whether the conditions required for activation are still satisfied. Rather, the defibrillation function remains fulfilled even if one of the conditions necessary for activation is no longer satisfied later.

If, on the other hand, it is determined during the test 250 that either an implanted RV electrode may no longer be detected any more or that no suitable signal conditions for a reliable activation of the defibrillation function are present after the specified time has elapsed, the test method reverts back to the cyclically performed electrode impedance measurement 210 in order to detect once again whether an electrode is connected to the defibrillator. It may be optionally provided that, for safety reasons, the already activated antibradycardia stimulation activity of the defibrillator remains activated. In this case—despite insufficient conditions for the safe performance of a defibrillation—the possibility of performing an antibradycardia stimulation and thus, if necessary, life-supporting measures for the patient would still be possible.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An implantable medical device comprising a processor and a memory unit, wherein the memory unit comprises a computer-readable program that causes the processor to perform the following steps when run on the processor:
    a) performing a detection to determine that the implantable medical device is in an implanted state; and
    b) activating a first diagnostic or therapeutic function of the implantable medical device, and subsequently activating a second diagnostic or therapeutic function of the implantable medical device, wherein the second diagnostic or therapeutic function is activated only after the fulfilment of: i) a passing of a function test; and ii) at least one of an elapse of a first time period from the activation of the first diagnostic or therapeutic function or an elapse of a second time period from the detection that the implantable medical device is in an implanted state;
    wherein the first diagnostic or therapeutic function and/or the second diagnostic or therapeutic function comprises a function for cardiac defibrillation, a function for antitachycardia stimulation of a cardiac region of a patient and/or a function for the automatic adaptation of algorithms used for antitachycardia stimulation.

2. The implantable medical device according to claim 1, wherein the implantable medical device is a device selected from the group consisting of pacemaker implants, cardioverter-defibrillators, cardiac resynchronisation therapy devices, spinal cord stimulators, deep brain stimulation devices and implantable drug pumps.

3. The implantable medical device according to claim 1, wherein the program causes the processor to activate the first diagnostic or therapeutic function only after a third time period has elapsed from the detection that the implantable medical device is in an implanted state.

4. The implantable medical device according to claim 1, wherein the first time period and/or the second time period each have a length which is between 5 minutes and 48 hours.

5. The implantable medical device according to claim 1, wherein the implantable medical device comprises a time-measuring device for measuring the first time period and/or the second time period.

6. The implantable medical device according to claim 5, wherein the program causes the processor to stop, change or reset the time-measuring device depending on a start event in order to start measuring the first time period and/or the second time period.

7. The implantable medical device according to claim 1, wherein the first diagnostic or therapeutic function and/or the second diagnostic or therapeutic function comprises a detection of a cardiac signal of a patient, a stimulation of a cardiac region of a patient within the scope of a pacemaker stimulation, a stimulation of a cardiac region of a patient within the scope of a cardiac resynchronisation therapy, a function for detecting an electrode error and/or an electrode dislocation and/or a function for remote implant monitoring.

8. The implantable medical device according to claim 1, wherein the implantable medical device is a cardiac resynchronisation therapy device or a cardioverter/defibrillator, and the second diagnostic or therapeutic function comprises a cardiac defibrillation function.

9. The implantable medical device according to claim 1, wherein the function test is selected from the group consisting of a test in order to determine whether electrodes of the implantable medical device provided for detecting electrical signals and/or emitting electrical pulses are correctly positioned, a test in order to determine whether electrodes provided for detecting electrical signals and/or emitting electrical pulses have an electrode breakage, a test in order to determine compliance with a signal quality criterion, and a test in order to determine the type of detected physiological electrical signals.

10. The implantable medical device according to claim 1, wherein the program causes the processor to determine available shock vectors following fulfilment of the activation criterion for a defibrillation function.

11. The implantable medical device according to claim 1, wherein the program causes the processor to activate all implanted defibrillation electrodes of the implantable medical device for defibrillation and for electrode diagnostics upon detection that the implantable medical device is in its implanted state.

12. A method for controlling the operation of an implantable medical device according to claim 1, comprising the following steps:
   a) performing a detection to determine that the implantable medical device is in an implanted state; and
   b) activating a first diagnostic or therapeutic function of the implantable medical device, and subsequently activating a second diagnostic or therapeutic function of the implantable medical device, wherein the second diagnostic or therapeutic function is activated only after the fulfilment of: i) a passing of a function test; and ii) at least one of an elapse of a first time period from the activation of the first diagnostic or therapeutic function or an elapse of a second time period from the detection that the implantable medical device is in an implanted state
wherein the first diagnostic or therapeutic function and/or the second diagnostic or therapeutic function comprises a function for cardiac defibrillation, a function for antitachycardia stimulation of a cardiac region of a patient and/or a function for automatic adaptation of algorithms used for antitachycardia stimulation.

13. A computer program product comprising a computer-readable code that causes a processor to perform the following steps when run on the processor:
   a) performing a detection to determine that an implantable medical device is in an implanted state; and
   b) activating a first diagnostic or therapeutic function of the implantable medical device, and subsequently activating a second diagnostic or therapeutic function of the implantable medical device, wherein the second diagnostic or therapeutic function is activated only after the fulfilment of: i) a passing of a function test; and ii) at least one of an elapse of a first time period from the activation of the first diagnostic or therapeutic function or an elapse of a second time period from the detection that the implantable medical device is in an implanted state
wherein the first diagnostic or therapeutic function and/or the second diagnostic or therapeutic function comprises a function for cardiac defibrillation, a function for antitachycardia stimulation of a cardiac region of a patient and/or a function for automatic adaptation of algorithms used for antitachycardia stimulation.

14. A method for implanting an implantable medical device according to claim 1 into a human or animal patient in need of such implantation, wherein the method comprises the steps of:
   a) implanting the implantable medical device into the patient;
   b) performing a detection to determine that the implantable medical device is in an implanted state by means of a program run on the processor;
   c) activating a first diagnostic or therapeutic function of the implantable medical device, and subsequently activating a second diagnostic or therapeutic function of the implantable medical device by means of a program run on the processor, wherein the second diagnostic or therapeutic function is activated only after the fulfilment of: i) a passing of a function test; and ii) at least one of an elapse of a first time period from the activation of the first diagnostic or therapeutic function or an elapse of a second time period from the detection that the implantable medical device is in an implanted state
wherein
the first diagnostic or therapeutic function and/or the second diagnostic or therapeutic function comprises a function for cardiac defibrillation, a function for antitachycardia stimulation of a cardiac region of a patient and/or a function for automatic adaptation of algorithms used for antitachycardia stimulation.

* * * * *